United States Patent
Hassler et al.

(10) Patent No.: US 12,246,110 B2
(45) Date of Patent: *Mar. 11, 2025

(54) IN VITRO METHOD FOR CREATING A VIABLE CONNECTIVE TISSUE AND/OR OSSEOUS TISSUE

(71) Applicant: TORNIER, Montbonnot Saint Martin (FR)

(72) Inventors: Michel Hassler, Saint Ismier (FR); Ghassene Ouenzerfi, Saint Martin d'Hères (FR)

(73) Assignee: TORNIER, Montbonnot Saint Martin (FR)

( * ) Notice: Subject to any disclaimer, the term of this patent is extended or adjusted under 35 U.S.C. 154(b) by 190 days.

This patent is subject to a terminal disclaimer.

(21) Appl. No.: 18/152,470

(22) Filed: Jan. 10, 2023

(65) Prior Publication Data

US 2023/0158207 A1    May 25, 2023

Related U.S. Application Data

(63) Continuation of application No. 16/772,712, filed as application No. PCT/EP2018/085148 on Dec. 17, 2018, now Pat. No. 11,577,000.

(30) Foreign Application Priority Data

Dec. 18, 2017 (EP) ..................... 17306796

(51) Int. Cl.
| | |
|---|---|
| A61L 27/36 | (2006.01) |
| C12M 1/00 | (2006.01) |
| C12M 1/42 | (2006.01) |
| C12M 3/00 | (2006.01) |
| C12N 5/077 | (2010.01) |

(52) U.S. Cl.
CPC ....... *A61L 27/3612* (2013.01); *A61L 27/3654* (2013.01); *A61L 27/3691* (2013.01); *C12M 21/08* (2013.01); *C12M 23/20* (2013.01); *C12M 35/04* (2013.01); *C12N 5/0654* (2013.01); *C12N 5/0655* (2013.01); *C12N 2527/00* (2013.01)

(58) Field of Classification Search
CPC ................................. A61L 27/3691
See application file for complete search history.

(56) References Cited

U.S. PATENT DOCUMENTS

| | | | |
|---|---|---|---|
| 4,846,840 | A | 7/1989 | Leclercq et al. |
| 4,968,623 | A | 11/1990 | Franks |
| 5,514,410 | A | 5/1996 | Ely et al. |
| 5,743,918 | A | 4/1998 | Calandruccio et al. |
| 2001/0039455 | A1 | 11/2001 | Simon et al. |
| 2001/0043918 | A1 | 11/2001 | Masini et al. |
| 2004/0133276 | A1 | 7/2004 | Lang et al. |
| 2006/0129071 | A1 | 6/2006 | Hauselmann et al. |
| 2008/0215156 | A1 | 9/2008 | Duggal et al. |
| 2009/0148876 | A1 | 6/2009 | Dodge |
| 2010/0161073 | A1 | 6/2010 | Thomas et al. |
| 2012/0215320 | A1 | 8/2012 | Harber et al. |
| 2013/0304226 | A1 | 11/2013 | Ritz et al. |
| 2014/0255364 | A1 | 9/2014 | Zeng et al. |

FOREIGN PATENT DOCUMENTS

| | | |
|---|---|---|
| EP | 2468217 B1 | 3/2016 |
| WO | 2004104188 A1 | 12/2004 |
| WO | 2007041375 A2 | 4/2007 |
| WO | 2008120215 A2 | 10/2008 |
| WO | 2009047045 A2 | 4/2009 |
| WO | 2013150537 A1 | 10/2013 |
| WO | 2019121481 A1 | 6/2019 |
| WO | 2019121578 A1 | 6/2019 |

OTHER PUBLICATIONS

Communication Pursuant to Article 94(3) issued in connection with European Patent Application No. 18819112.6, Jan. 30, 2024, 7 pages.
International Search Report and Written Opinion dated Jun. 27, 2019 in International Patent Application No. PCT/EP2008/085148.
International Search Report and Written Opinion dated Dec. 17, 2018 In PCT/EP2018/085329, 12 pages.
Non-Final Office Action dated Nov. 16, 2021 in U.S. Appl. No. 16/772,595.
Final Office Action dated Apr. 25, 2022 in U.S. Appl. No. 16/772,595.
Shahin, et al, Biotechnology and Bioengineering, 2012; 109: 1060-1073, published online Nov. 17, 2011 (Year: 2011).
Meinert, et al., Scientific Reports, 7: 16997, pp. 1-14, published online Dec. 5, 2017 (Year: 2017).
Xue, et al., Expert Opinion on Biological Therapy 15:5, 623-632 (2015)(Year: 2015).
Klein, et al., Soft Matter 6, 5175-5183 (2020)(Year: 2010).

*Primary Examiner* — Evelyn Y Pyla
(74) *Attorney, Agent, or Firm* — DUANE MORRIS LLP

(57) ABSTRACT

The present invention relates to an in vitro method for creating a viable connective tissue and/or osseous tissue obtained by tribological solicitations of a biological culture. It further relates to a viable connective tissue and/or osseous tissue susceptible to be obtained by said method as well as to the use of said method or viable connective tissue and/or osseous tissue to prepare a biological implant.

11 Claims, 1 Drawing Sheet

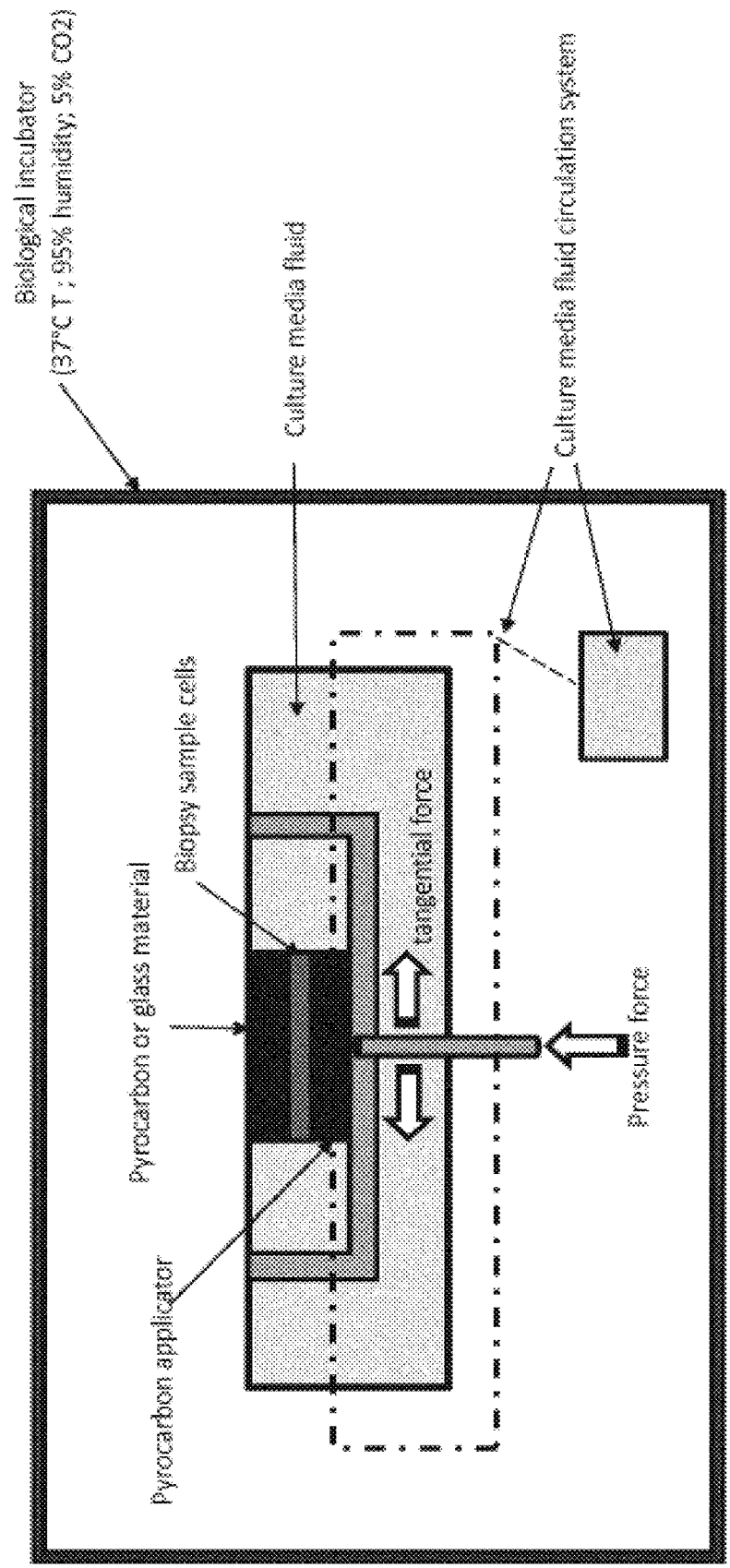

IN VITRO METHOD FOR CREATING A VIABLE CONNECTIVE TISSUE AND/OR OSSEOUS TISSUE

CROSS-REFERENCE TO RELATED APPLICATIONS

This application is a continuation of co-pending U.S. patent application Ser. No. 16/772,712, filed on Jun. 12, 2020 as a U.S. national phase application of PCT/EP2018/085148, filed on Dec. 17, 2018, which claims priority to European Patent Application No. 17306796.8, filed on Dec. 18, 2017, the entire contents of which are incorporated by reference herein.

FIELD

The present invention relates to an in vitro method for creating a viable connective tissue and/or osseous tissue obtained by tribological solicitations of a biological culture. It further relates to a viable connective tissue and/or osseous tissue susceptible to be obtained by said method as well as to the use of said method or viable connective tissue and/or osseous tissue to prepare a biological implant.

BACKGROUND OF THE INVENTION

Current treatment of cartilage lesions or damage can follow two following paths.

The first one is prosthetic treatment: prosthesis (total or hemi) provide a good solution for short or middle term. But for young patients, none of them provide a definitive solution and reoperation risks and bone/cartilage stock management are a concern.

The second one is reconstructive treatment of cartilage. It can be a debridment and abrasion arthroplasty which is not a real reparative procedure or a subchondral drilling and microfracture which results in poor integration of fibrocartilage with surrounding articular cartilage and is not satisfactory. Osteochondral allograft is also an option. It causes however cell viability and contamination issues. Mosaicplasty is also conducted but leads to morbidity of donor site and technical issues. Last one is autologous chondrocyte culture in a scaffold. This last option causes medial and long term viability concern but seems to be the more promising one. As of today, it still fails because of the degradation of the long term mechanical and biological properties and the poor clinical results.

There is thus a need to provide solutions overcoming all these issues and concerns.

BRIEF DESCRIPTION OF DRAWINGS

FIG. 1: Picture of an example of installation.

DETAILED DESCRIPTION OF THE INVENTION

It has been surprisingly found by the inventors that starting from a blood sample or biopsy from a patient, their cultivation in a bioreactor creates a fibrous tissue that, upon specific tribological solicitations by a pyrocarbon applicator will lead to a viable connective tissue and/or osseous tissue.

It has been found that the physic-chemical properties of the pyrocarbon material transfer these solicitations in such a manner that it reproduces the natural phenomenon of creation of connective tissue and/or osseous tissue.

This could allow the patient to receive a strong and viable patch of cartilage that the surgeon will implant to repair the local defect.

The present invention thus relates to an in vitro method for creating a viable connective tissue and/or osseous tissue obtained by tribological solicitations of a biological culture, wherein: (a) a blood sample or biopsy from a patient is cultured on the surface of a pyrocarbon (Pyc) applicator in the presence of a tissue culture media in a bioreactor for at least 4 days, and concomitantly, after or with an overlap, (b) the growing tissue obtained at step (a) is submitted to tribological solicitations for at least 4 days; wherein: the growing tissue obtained at step (a) is submitted to a perpendicular pressure force to obtain a osseous tissue; and/or the growing tissue obtained at step (a) is submitted to a perpendicular pressure force and a movement parallel to the surface of said pyrocarbon applicator to obtain a connective tissue.

In particular, in the method according to the invention, step (b) is conducted using a material selected from the group consisting of polymers, ceramics and combinations thereof, the growing tissue being positioned between said material and the pyrocarbon applicator, the pyrocarbon applicator and the material applying the perpendicular pressure force on said tissue. More particularly, the growing tissue is positioned between the surface of said material and the surface of said pyrocarbon applicator.

Still particularly, in the method according to the invention, step (b) comprises: a step (b0) in which the growing tissue obtained at step (a) is submitted to a perpendicular pressure force for at least 4 days; and concomitantly, after or with an overlap, a step (b1) in which the growing tissue obtained at step (a) and/or the osseous tissue obtained at step (b0) is submitted to a perpendicular pressure force and a movement parallel to the surface of said pyrocarbon applicator for at least 4 days.

Even more particularly, step (b) comprises: a step (b0) in which the growing tissue obtained at step (a) is positioned between a material selected from the group consisting of polymers, ceramics and combinations thereof and the pyrocarbon applicator, the pyrocarbon applicator and the material applying the perpendicular pressure force on said tissue; and concomitantly, after or with an overlap, a step (b1) in which the growing tissue obtained at step (a) and/or the osseous tissue obtained at step (b0) is submitted to a perpendicular pressure force and a movement parallel to the surface of said pyrocarbon applicator.

By "viable connective tissue and/or osseous tissue" is meant a tissue viable for surgery, in particular a cartilage graft when connective tissue is contemplated, whatever its stage of development, and a bone graft when an osseous tissue is contemplated, in particular cortical bone graft. This means in particular that the tissue/graft can be cultured and then can be implanted. Once implanted in the same patient, a viable graft is autologous and it fulfills the function for which it has been implanted, e.g. fulfills the function of cartilage for a cartilage graft. In the context of the present invention, implantation in another patient in the form of a homologous viable graft is also contemplated.

In one embodiment, the method described herein is for creating a viable autologous connective tissue and/or osseous tissue.

In the context of the present invention, "growing tissue" is a generic term, and can cover any form of cells arrangement, for example: bone, cartilage, ligaments.

A "biopsy" as described herein is for example a biopsy from the place of cartilage and/or bone defect or next to it. It can be for example a biopsy of shoulder's cartilage, knee cartilage, hip cartilage or nose cartilage. It can also be taken from the patient in an area not near the defect, but where it is classical to harvest bone cells without secondary effects, like of the iliac crest or of the head of the distal radius. According to the invention, it may be obtained from the patient by any appropriate means of sampling known by the person skilled in the art.

A "blood sample" as described herein includes whole blood, plasma, serum, circulating epithelial cells, constituents, or any derivative of blood sample. The blood sample according to the invention may be obtained from the subject by any appropriate means of sampling known by the person skilled in the art.

In particular, in the method described herein, the blood sample or biopsy of the patient includes cells, in particular stem cells and/or cells aggregates. For example said cells can be chondrocytes and/or fibroblasts. More particularly, the method described herein comprises a step (a0) consisting in isolating the cells, in particular stem cells and/or cells aggregates from the blood sample or biopsy, and further using said isolated cells or stem cells or cells aggregates in step (a).

For example, the method described herein comprises a step (a0) consisting in isolating chondrocytes and/or fibroblasts, in particular chondrocytes and/or fibroblasts from a biopsy, and further using said isolated chondrocytes and/or fibroblasts in step (a).

Said cells, in particular stem cells or cells aggregates, can be isolated by any method known by the skilled person. In particular, the stem cells from the blood sample can be isolated using a process such as centrifugation.

For example, stem cells can be isolated from the extracellular matrix contained in the patient's blood. Multiplication (amplification) of the cells making to obtain a sufficient number of cells can then be done by routine methods.

By "patient" is meant a warm-blooded animal such as a mammal, animal or human, in particular a human, which needs or is susceptible to need a viable connective tissue and/or osseous tissue, in particular a viable cartilage and/or bone graft. "Subject" can be used indifferently instead of "patient".

A "pyrocarbon applicator" or "Pyc" according to the invention is a surface made of or covered by Pyrocarbon. Pyrocarbon is a well-known material, used for many years to manufacture heart valves components and orthopedic implants. Pyrocarbon is a carbon material coating deposited on a graphite substrate heated to 1400° C. in a special reactor, and placed into a condition of weightlessness by injecting gas at appropriate flow from bottom to top on a vertical pipe. Gas injected will be a mix of neutral gas and hydrocarbon gas such as propane. In the absence of oxygen, carbon and hydrogen bonds of a hydrocarbon gas are broken at the temperature of about 1400° C. Hydrogen atoms will recombine into hydrogen gas, and carbon atoms will recombine into a thick layer that will cover the graphite substrate. The structure of the carbon layer is well known and described in the literature as turbostratic Pyrocarbon which can be pure, or silicon alloyed. Percentage of silicon carbide included in the alloyed Pyrocarbon could be up to 12% in weight. Pyrocarbon and process for depositing pyrocarbon coatings are, for example, described in U.S. Pat. No. 5,514,410. In particular, said pyrocarbon applicator will be made or covered by pure Pyrocarbon. This pyrocarbon applicator is commercially available and is sold by the company Wright® (Memphis, Tenn.).

In particular, the pyrocarbon applicator used in the method described herein is flat or a matched convex/concave shape. This convex or concave shape will be mimicking the shape of the patients articulation where the bone defect is present, so that to allow the preparation of a connective tissue osseous tissue that will match the patients shape to repair.

The tissue culture media according to the invention is for example DMEM (Dulbecco/Vogt modified Eagle's minimal essential medium) with FBS (Foetal bovine serum).

In particular, the tissue culture media used in the method according to the invention comprises synovial fluid components. Phospholipids can be cited as examples of synovial fluids components according to the invention. These components allow that proper sliding of substrate surfaces against each other will occur.

In one embodiment, the tissue culture media used also comprises ascorbic acid and/or β-glycerophosphate, in particular when creation of osseous tissue is contemplated.

In one embodiment, the tissue culture media used does not comprise ascorbic acid and β-glycerophosphate, in particular when creation of connective tissue is contemplated.

The growing tissue as mentioned in step (b) is the tissue resulting from the culture of the blood sample or the biopsy from the patient, under the conditions mentioned in step (a). It can be in particular a fibrous tissue.

The "biological culture" as described herein comprises components that can evolve depending on the stage of the method according to the invention. Indeed, the culture can first comprise a blood sample or biopsy from a patient or cells, in particular stem cells, and/or cells aggregates isolated from said blood sample and/or biopsy and a tissue culture media, blood sample or biopsy or cells or cells aggregates derived therefrom, will grow into a growing tissue, in particular a fibrous tissue (step (a)) and then into a osseous tissue and/or connective tissue (step (b)). For example, when the blood sample or biopsy of the patient includes stem cells, a stem cell aggregate, or a biological support (like constructions of hyaluronan-gelatin for example) which will be seeded by the stem cells can be used.

During step (a), blood sample or biopsy or cells, in particular stem cells, and/or cells aggregates isolated therefrom can be cultured in an appropriate culture medium. It can be determined by the skilled person. In particular, said culture medium comprises synovial fluid components as previously mentioned. Mention can be made for example of the following culture medium: Dulbecco's Modified Eagle Medium DMEM, 4.5 g/L glucose, 100 mM HEPES, 100 U/mL penicillin and 100 µg/mL streptomycin, 10% Foetal Bovine Serum (FBS) and some other synovial and nutrition elements.

During step (b), the growing tissue obtained at step (a) and/or the osseous tissue obtained at step (b0) can be maintained in culture in another culture medium. It can be determined by the skilled person, mention can be made for example of the following culture medium: Dulbecco's Modified Eagle Medium (DMEM), 1 g/L glucose (4.5 g/L for osseous tissue growing), 100 U/mL penicillin and 100 µg/mL streptomycin, 10% Foetal Bovine Serum and some other synovial (like DDPC lipids and Hyaluronic acid) and nutrition elements (Ham's F12-nutrient mixture solution).

By "tribological solicitations" is meant the meaning known in the art. In the context of the invention, it includes a perpendicular pressure force and optionally a movement parallel to the surface of said pyrocarbon applicator, depending on the type of viable graft the skilled person intends to obtain. In the context of the invention, a shear force can be for example mentioned.

By "perpendicular pressure force" is meant the meaning known in the art. In the context of the invention, a compression movement can be for example mentioned. In particular, said perpendicular pressure force can be not constant i.e. its amplitude can vary, resulting in a force which is for example pulsed or cycled.

In the scope of the invention, "perpendicular pressure force" is similar with "normal force."

By "a movement parallel to the surface of said pyrocarbon applicator" is meant the meaning known in the art. In the context of the invention, movement parallel to the surface, of said pyrocarbon applicator, combined with the perpendicular pressure force to generate a shear or tangential force can be for example mentioned. For example, the shear force can be generated by oscillation and/or rotation of said pyrocarbon applicator as described herein with respect to the material as described herein.

These force/movement can be generated by a mechanical simulator, in an incubator allowing the cultivation of cells for several weeks. The incubator (bioreactor) and mechanical simulator to use in the context of the present invention can be chosen by the skilled person on the basis of his current knowledge. Reference may be made for example to Elder et al 2001 and Elder et al 2000.

Parameters to be controlled will be determined by the skilled person on the basis of its current knowledge. Examples of mechanical constraints (shaking, mechanical solicitation), intake of growth factors and nutrients, oxygen and $CO_2$ levels are shown in Table 1 of the experimental part.

In the context of the invention, the material selected from the group consisting of polymers, ceramics and combinations thereof can in particular be a plastic or glass surface, and more particularly be transparent. These materials allow to visualize the growth of the graft through it, and by this visualization control and monitor the parameters.

In one embodiment, said material is a pyrocarbon material. Said material does not allow visual inspection i.e. to visually follow the evolution of the growing tissue, but generates faster growth. It will be preferred when parameters are already mastered.

As can be deduced from the method described herein, the different steps of the methods can be conducted at the same time (concomitantly), one after the other (after) or one step can start before the end of the first one (with an overlap).

In addition, step (b) can be conducted differently depending on the type of viable tissue, in particular, viable graft, it is intended to obtain (i.e. a connective tissue and/or osseous tissue, in particular, a cartilage and/or bone graft).

The method according to the invention can thus cover the following different embodiments. (1) An in vitro method for creating a viable osseous tissue obtained by tribological solicitations of a biological culture, wherein: (a) a blood sample or biopsy from a patient is cultured on the surface of a pyrocarbon (Pyc) applicator in the presence of a tissue culture media in a bioreactor for at least 4 days, and concomitantly, after or with an overlap (b) the growing tissue obtained at step (a) is submitted to a perpendicular pressure force for at least a 4 days. (2) An in vitro method for creating a viable connective tissue obtained by tribological solicitations of a biological culture, wherein: (a) a blood sample or biopsy from a patient is cultured on the surface of a pyrocarbon (Pyc) applicator in the presence of a tissue culture media in a bioreactor for at least 4 days, and concomitantly, after or with an overlap (b) the growing tissue obtained at step (a) is submitted to a perpendicular pressure force and a movement parallel to the surface of said pyrocarbon applicator for at least 4 days. (3) An in vitro method for creating osseous tissue covered with viable connective tissue obtained by tribological solicitations of a biological culture, wherein: (a) a blood sample or biopsy from a patient is cultured on the surface of a pyrocarbon (Pyc) applicator in the presence of a tissue culture media in a bioreactor for at least 4 days, and concomitantly, after or with an overlap (b0) the growing tissue obtained at step (a) is submitted to a perpendicular pressure force for at least 4 days, and concomitantly, after or with an overlap (b1) the growing tissue obtained at step (a) and/or the osseous tissue obtained at step (b0) is submitted to a perpendicular pressure force and to a movement parallel to the surface of said pyrocarbon applicator for at least 4 days.

In the first embodiment, a viable osseous tissue is obtained.

In the second one, a viable connective tissue is obtained.

In the third one, a viable connective tissue is obtained, but due to the perpendicular pressure force applies, it can be a viable connective tissue covering viable osseous tissue.

As mentioned herein, the duration of each step is variable and is of at least 4 days, in particular of at least 4 days, for example is of between 4 and 10 days or between 4 and 20 days, for example of 4, 5, 6, 7, 8, 9, 10, 15, 17 or 20 days. The man skilled in the art will be able to adapt these durations on the basis of its general knowledge.

When at least for 4 days are mentioned for steps (b0) and (b1), it has to be understood that the sum of duration of each step is at much of about 20 days, preferably at much of 20 days.

In particular, in the method according to the invention, each step of the method is conducted for between 4 and 10 days.

The present invention also relates to a viable connective tissue and/or osseous tissue susceptible to be obtained by the method described herein.

In particular, said viable connective tissue and/or osseous tissue is obtained by the method described herein.

The present invention further relates to the use of the method described herein or of the viable connective tissue and/or osseous tissue described herein to prepare a biological implant.

It also relates to a method for preparing a biological implant comprising the creation of viable connective tissue and/or osseous tissue by the steps of the method described therein.

By "biological implant" is meant the normal meaning of these terms for a skilled person. It relates in particular to a medical device manufactured to replace a missing biological structure, support a damaged biological structure, or enhance an existing biological structure. In particular, said biological implant is a resurfacing cap, a sheet of cartilage or an entire articular end of a bone.

The present invention further relates to the use of a biological implant as described herein to repair a localized cartilage defect on an articular surface.

It also relates to a biological implant as described herein for use to repair a localized cartilage defect on an articular surface.

It also relates to method for repairing a localized cartilage defect on an articular surface comprising the implantation of a biological implant as described herein at the place of the defect.

In particular, said defect has been abraded and covered by the biological implant.

The present invention also relates to a bioreactor comprising a pyrocarbon (Pyc) applicator, as described herein. In particular, it relates to the combined use of a bioreactor and a pyrocarbon (Pyc) applicator, as described herein, for creating a viable connective tissue and/or osseous tissue according to the invention.

The invention will be further illustrated by the following figures and examples.

EXAMPLES

Cartilage tissue has been grown in vitro from stem cells (extracted from the patient's blood) and is intended to be implanted.

Obtaining cartilage tissue has required several steps: Isolation of stem cells from the extracellular matrix contained in the patient's blood. Multiplication (amplification) of the cells making to obtain a sufficient number of cells. Forming a stem cell aggregate, or developing a biological support (like constructions of hyaluronan-gelatin for example) which will be seeded by the stem cells. Mechanical (and biochemical) stimulation of the biological culture containing the cells (or the stem cell aggregate) in shear and compression against a Pyrocarbon disk in a mechanical simulator, in an incubator allowing the cultivation of cells for several weeks. Many parameters had to be controlled: mechanical constraints (shaking, mechanical solicitation), intake of growth factors and nutrients, oxygen and $CO_2$ levels as shown in Table 1 below.

TABLE 1

| Criteria | Level |
| --- | --- |
| Normal Force applied | 1N < F < 70N |
| Normal Force frequency | 0.1 Hz < f < 10 Hz |
| Tangential force frequency | 0.1 Hz < f < 10 Hz |
| Torque applied | 0.001N · m < C < 1N · m |
| Physical/chemical environment | 37° 5% $CO_2$ |
| Pyrocarbon applicator | Graphite disks (1 mm thick, diam 20 mm) covered with 200 μm of PyC, polished at Ra 0.03 μm |
| Cells culture media for cells culture step (step (a)) | Dulbecco's Modified Eagle Medium DMEM, 4.5 g/L glucose, 100 mM HEPES and 10% FBS (still containing L-glutamine, penicillin and streptomycin) |
| Cells culture media during mechanical step (step (b)) | Dulbecco's Modified Eagle Medium (DMEM) containing 20 mM L-glutamine, 1 g/L glucose, 100 U/mL penicillin and 100 μg/mL streptomycin, 10% Foetal Bovine Serum (FBS) + synovial components |

Results obtained by this setting have provided a cortical graft covered with articular cartilage layer, proven by specific histological and immunohistological staining.

These analyses showed the existence of biological tissue adherent to the bone.

Specific histological and immunohistological staining indicate that the surface layer of this tissue has the characteristics of cartilaginous tissue.

The invention claimed is:

1. An in vitro method for creating a viable connective tissue and/or osseous tissue obtained by tribological solicitations of a biological culture to repair a patient's bone defect, the method comprising:
   (a) culturing a blood sample or biopsy from the patient on a pyrocarbon (Pyc) applicator in the presence of a tissue culture media in a bioreactor for at least about 4 days thus resulting in tissue that is growing, wherein the Pyc applicator has a matched convex/concave shape that mimics a shape of the patient's bone defect to be repaired, and concomitantly, afterwards, or with an overlap of, wherein the blood sample or biopsy of the patient includes stem cells;
   (b0) submitting the growing tissue obtained at step (a) to a perpendicular pressure force for at least 4 days to obtain an osseous tissue, and concomitantly, after or with an overlap;
   (b1) submitting the growing tissue obtained at step (a) and the osseous tissue to a perpendicular pressure force and a movement parallel to a surface of the pyrocarbon applicator for at least 4 days to obtain a connective tissue; and
   (c) preparing a biological implant.

2. The method of claim 1, wherein the step (b0) is conducted using a material selected from the group consisting of polymers, ceramics, and combinations thereof, wherein the growing tissue being positioned between the material and the pyrocarbon applicator, the pyrocarbon applicator and the material applying the perpendicular pressure force on the tissue.

3. The method of claim 2, wherein the material selected from the group consisting of polymers, ceramics, and combinations thereof is a pyrocarbon material.

4. The method of claim 1, wherein the step (b1) is conducted using a material selected from the group consisting of polymers, ceramics, and combinations thereof, wherein the growing tissue and the osseous tissue are positioned between the material and the pyrocarbon applicator, the pyrocarbon applicator and the material applying the perpendicular pressure force and the movement parallel to the surface of the pyrocarbon applicator.

5. The method of claim 4, wherein the material selected from the group consisting of polymers, ceramics, and combinations thereof is pyrocarbon material.

6. The method of claim 1, wherein each step of the method is conducted for between 4 and 10 days.

7. The method of claim 1, comprising a step (a0) consisting in isolating the stem cells from the blood sample or biopsy, and further using said isolated stem cells in step (a).

8. The method of claim 1, wherein the tissue culture media comprises synovial fluid components.

9. The method of claim 1, wherein the biological implant is a resurfacing cap, a sheet of cartilage, or an entire articular end of a bone.

10. The method of claim 1, wherein the biological implant is configured to repair a localized cartilage defect on an articular surface.

11. The method of claim 10, wherein the defect has been abraded and covered by the biological implant.

* * * * *